US012082972B2

(12) United States Patent
Duval et al.

(10) Patent No.: US 12,082,972 B2
(45) Date of Patent: Sep. 10, 2024

(54) DEVICES, SYSTEMS, AND METHODS FOR REDUCING SIGNAL NOISE IN ENDOSCOPIC ROTATIONAL IMAGING

(71) Applicant: BOSTON SCIENTIFIC SCIMED INC., Maple Grove, MN (US)

(72) Inventors: George Wilfred Duval, Sudbury, MA (US); Laura Emily Richards, Worcester, MA (US); James J. Scutti, Norwell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 44 days.

(21) Appl. No.: 17/748,237

(22) Filed: May 19, 2022

(65) Prior Publication Data
US 2022/0370036 A1 Nov. 24, 2022

Related U.S. Application Data

(60) Provisional application No. 63/190,421, filed on May 19, 2021.

(51) Int. Cl.
*A61B 8/12* (2006.01)
*A61B 8/00* (2006.01)
*A61M 25/01* (2006.01)

(52) U.S. Cl.
CPC ............... *A61B 8/12* (2013.01); *A61B 8/445* (2013.01); *A61M 25/0138* (2013.01)

(58) Field of Classification Search
CPC .. A61B 8/12; A61B 8/445; A61B 8/56; A61B 8/00; A61M 25/0138; A61M 25/00
See application file for complete search history.

(56) References Cited

U.S. PATENT DOCUMENTS 4,954,793 A * 9/1990 Misu ............... H03H 9/72
  333/133
6,017,312 A * 1/2000 Masters ............ A61B 8/12
  600/462

(Continued)

OTHER PUBLICATIONS

International Search Report and Written Opinion dated Sep. 15, 2022 for International Application No. PCT/US2022/030000.

(Continued)

*Primary Examiner* — Pascal M Bui Pho
*Assistant Examiner* — Michael Yiming Fang
(74) *Attorney, Agent, or Firm* — Seager, Tufte & Wickhem, LLP

(57) ABSTRACT

The present disclosure includes devices, systems, and methods for reducing signal noise in endoscopic rotational imaging. Many embodiments include an elongate member that includes an impedance matching network disposed between a proximal imaging core and a distal imaging core. In many such embodiments, the elongate member may connect a controller at the proximal end and include a rotational transducer at the distal end. In various embodiments, the proximal and distal imaging cores may include a plurality of insulated conductors disposed within a shield (e.g., a shielded twisted pair (STP)). In various such embodiments, the insulated conductors may be utilized to communicate differential signals between the controller and the rotational imaging transducer. In some embodiments, the insulated conductors in the proximal imaging core may have a larger diameter than the insulated conductors in the distal imaging core.

20 Claims, 10 Drawing Sheets

(56) References Cited

U.S. PATENT DOCUMENTS

| | | | |
|---|---|---|---|
| 2004/0193057 A1 | 9/2004 | Barbato et al. | |
| 2009/0270737 A1* | 10/2009 | Thornton | A61B 8/445 600/466 |
| 2009/0275838 A1* | 11/2009 | Marshall | A61B 8/12 600/463 |
| 2014/0171803 A1* | 6/2014 | Van Hoven | A61B 8/445 600/467 |
| 2014/0316269 A1* | 10/2014 | Zhang | A61B 8/4209 602/1 |
| 2015/0141834 A1* | 5/2015 | Minemoto | C04B 35/462 29/25.35 |
| 2017/0290568 A1* | 10/2017 | Ko | A61B 8/4272 |
| 2019/0254506 A1* | 8/2019 | Hamm | A61M 25/0662 |
| 2022/0257196 A1* | 8/2022 | Massmann | A61B 5/6885 |
| 2022/0346750 A1* | 11/2022 | Robinson | A61B 8/445 |

OTHER PUBLICATIONS

Wang et al., "A High-Tolerance Matching Method Against Load Fluctuation for Ultrasonic Transducers," IEEE Transactions on Power Electronics, 35(1): 1147-1155, Jan. 2020.

Wei et al., Design of an automatic impedance matching circuit based on frequency tracking of ultrasonic transducer, IEEE 5th Information Technology and Mechatronics Engineering Conference, pp. 162-165, 2020.

* cited by examiner

DEVICES, SYSTEMS, AND METHODS FOR REDUCING SIGNAL NOISE IN ENDOSCOPIC ROTATIONAL IMAGING

FIELD

The present disclosure relates generally to the field of endoscopic rotational imaging. In particular, the present disclosure relates to devices, systems, and methods to reduce signal noise in endoscopic rotational imaging.

BACKGROUND

A variety of medical devices are positioned within a body lumen for diagnostic or therapeutic purposes. For example, an endoscopy is a procedure using an endoscope to look inside a body. Typically, an endoscopy procedure utilizes an elongate member (e.g., an endoscope) to access, examine, or interact with the interior of a hollow organ or cavity of a body for diagnostic or therapeutic purposes. The endoscope typically has direct visualization for viewing inside the body and/or may be equipped with ultrasound view capability. Such scopes have a profile diameter that allow the scope to be inserted into larger body lumens (e.g., gastrointestinal (GI) tract or trachea) of a certain diameter. For example, one type of endoscope, a bronchoscope can be used for visualizing the inside of the airways, up to a certain generation of airway having a diameter that can accommodate the diameter of the bronchoscope, for diagnostic and therapeutic purposes. The bronchoscope is inserted into the airways, such as through a mouth, nose, or tracheostomy. This may allow the practitioner to examine the patient's airways for abnormalities such as foreign bodies, bleeding, tumors, or inflammation. Sometimes a biopsy may be taken from inside the lungs. At a certain higher generations of airways, the diameter of the airway becomes too narrow to accommodate conventional endoscopes, which presents the challenge for improved devices having means to accurately navigate, locate, and biopsy tissue within these smaller airways or within other lumens of minimal diameter.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one aspect, the present disclosure relates to a medical device comprising a hub, a proximal imaging core, a distal imaging core, and an impedance matching network. The hub may include a connector and a rotational transformer having first and second ends, the first end may be coupled to the connector and the connector may be configured to couple with a controller. The proximal imaging core may have first and second ends and the first end of the proximal imaging core may be coupled to the second end of the rotational transformer. The distal imaging core may have first and second ends, and the second end of the distal imaging core may be coupled to a rotational imaging transducer. The impedance matching network may be coupled between the second end of the proximal imaging core and the first end of the distal imaging core.

In some embodiments, the rotational imaging transducer comprising a rotational ultrasound transducer. In various embodiments, the proximal imaging core may comprise a proximal drive cable and a first shielded twisted pair (STP) of a first diameter and the distal imaging core may comprise a distal drive cable and a second STP of a second diameter. In various such embodiments, the first STP is disposed within the proximal drive cable and the second STP is disposed within the distal drive cable. In some such embodiments, the proximal imaging core is disposed within a proximal catheter section and the distal imaging core is disposed within a distal catheter section. In further such embodiments, the proximal catheter section is coupled to the distal catheter section via a telescoping joint. In many such embodiments, the first diameter corresponds to 42-50 American wire gauge (AWG) and the second diameter corresponds to 46-52 AWG. In several embodiments, the proximal imaging core, the distal imaging core, and the impedance matching network are disposed within a telescoping sheath. In some embodiments, the impedance matching network comprises an inductor and a capacitor. In various such embodiments, the inductor and capacitor are electrically connected in parallel. In some such embodiments, the inductor is between 170 and 210 nanohenry and the capacitor is between 40 and 60 picofarad. In many embodiments, the impedance matching network comprises a characteristic impedance between 55 and 75 ohms. In various embodiments, the distal imaging core includes a plurality of signal conductors. In various such embodiments, the impedance matching network includes an inductor-capacitor matching circuit for each of the plurality of signal conductors.

In another aspect, the present disclosure relates to a system, which may comprise a hub, a controller, a proximal imaging core, a distal imaging core, and an impedance matching network. The hub may include a connector and a rotational transformer having first and second ends, the first end may be coupled to the connector and the connector may be configured to couple with the controller. The proximal imaging core may have first and second ends and the first end of the proximal imaging core may be coupled to the second end of the rotational transformer. The distal imaging core may have first and second ends, and the second end of the distal imaging core may be coupled to a rotational imaging transducer. The impedance matching network may be coupled between the second end of the proximal imaging core and the first end of the distal imaging core.

In some embodiments, the impedance matching network comprises an inductor between 170 and 210 nanohenry and a capacitor between 40 and 60 picofarad. In various embodiments, the impedance matching network comprises a characteristic impedance between 55 and 75 ohms. In several embodiments, the distal imaging core includes a plurality of signal conductors. In several such embodiments, the impedance matching network includes an inductor-capacitor matching circuit for each of the plurality of signal conductors.

In yet another aspect, the present disclosure relates to a method. The method may include inserting a distal imaging core into a body lumen. The distal imaging core may have first and second ends, the second end of the distal imaging core may be coupled to a rotational imaging transducer, the first end of the distal imaging core may be coupled to an impedance matching network, the impedance matching network may be coupled to a proximal imaging core. The method may further include generating a radial image with the rotational imaging transducer.

In some embodiments, the impedance matching network comprises an inductor between 170 and 210 nanohenry and a capacitor between 40 and 60 picofarad. In many embodiments, the impedance matching network comprises a characteristic impedance between 55 and 75 ohms. In various embodiments, the distal imaging core includes a plurality of signal conductors. In various such embodiments, the impedance matching network includes an inductor-capacitor matching circuit for each of the plurality of signal conductors.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. In will be appreciated that various figures included in this disclosure may omit some components, illustrate portions of some components, and/or present some components as transparent to facilitate illustration and description of components that may otherwise appear hidden. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
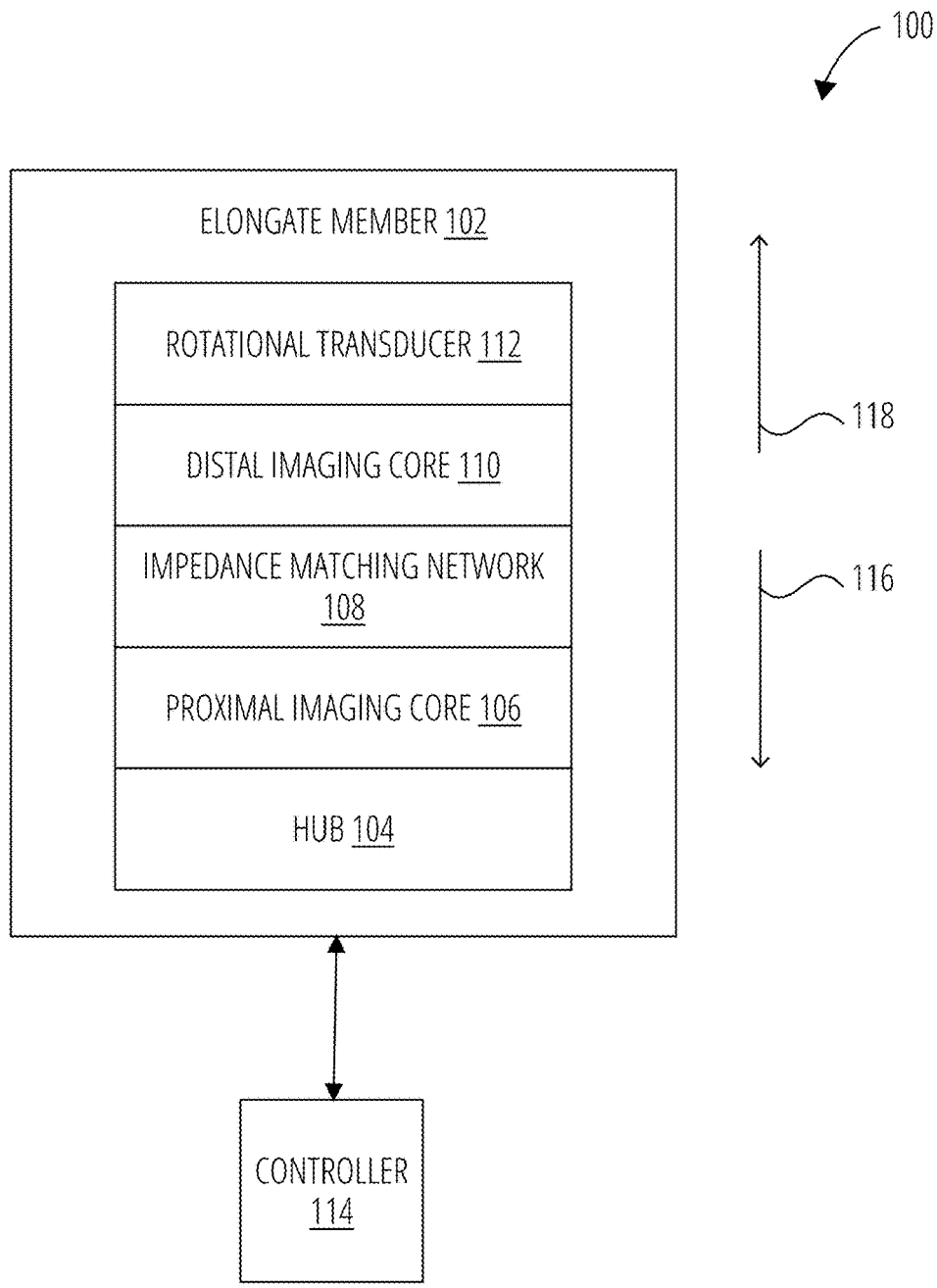
FIG. 1A illustrates an exemplary medical imaging device according to one or more embodiments disclosed hereby.

The present disclosure relates generally to devices, systems, and methods for endoscopic rotational imaging, such as rotational ultrasound biomicroscopy (UBM). Some embodiments are particularly directed to reducing signal noise in endoscopic rotational imaging. Many embodiments include an elongate member that includes an impedance matching network disposed between a proximal imaging core and a distal imaging core. In many such embodiments, the elongate member may connect a controller at the proximal end and include a rotational transducer at the distal end. In various embodiments, the proximal and distal imaging cores may include a plurality of insulated conductors disposed within a shield (e.g., a shielded twisted pair (STP)). In various such embodiments, the insulated conductors may be utilized to communicate differential signals between the controller and the rotational imaging transducer. In some embodiments, the insulated conductors in the proximal imaging core may have a larger diameter than the insulated conductors in the distal imaging core. In some such embodiments, the impedance matching network may match impedance between the proximal and distal imaging cores. These and other embodiments are described and claimed.

Challenges face endoscopic rotational imaging, such as excessive noise (e.g., electromagnetic (EM) interference). Excessive noise can reduce, or prevent, the ability to generate a clear image. For example, rotational UBM devices are susceptible to coupling noise in the 20-60 megahertz (MHz) spectrum. This coupling noise may be due, at least in part, to the length of the imaging core and strong shield coupling to the signal. In some embodiments, a single ended coaxial cable may be used in the imaging core. However, the outer conductor of the coaxial cable may be utilized to act as a signal carrier and a shield, such as due to size constraints, leading to high susceptibility for signal noise, such as from hospital bed electronics and other ambient sources. Adding further complexity, utilizing STPs can be challenging due, at least in part, to space constraints and balancing the trade-off of an increase in characteristic cable impedance and a smaller diameter signal conductor. Such limitations can reduce the usability and applicability of endoscopic rotational imaging devices, contributing to inefficient devices with sub-optimal capabilities. It is with these considerations in mind that a variety of advantageous medical outcomes may be realized by the devices, systems, and methods of the present disclosure.

The following detailed description should be read with reference to the drawings, which depict illustrative embodiments. The present disclosure is not limited to the particular embodiments described, as such embodiments may vary. The terminology used herein is for the purpose of describing particular embodiments only and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like. The structures and configurations, and methods of deploying, in order to stabilize, maintain, and/or otherwise facilitate fluid flow paths may find utility beyond treatments discussed herein.

As used herein, "proximal end" refers to the end of a device that lies closest to the user (medical professional or clinician or technician or operator or physician, etc., such terms being used interchangeably herein without intent to limit, and including automated controller systems or otherwise) along the device when introducing the device into a patient, and "distal end" refers to the end of a device or object that lies furthest from the user along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges or values by endpoints includes all numbers within that range, including the endpoints (e.g. 1 to 5 includes 1, 1.5, 2, 2.75, 3, 3.80, 4, and 5), and fractions thereof.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1A illustrates a medical imaging device 100 according to one or more embodiments disclosed hereby. Medical imaging device 100 includes an elongate member 102 and a controller 114. The elongate member 102 may include a proximal end 116 and a distal end 118. Moving from the proximal end 116 to the distal end 118, the elongate member 102 includes a hub 104, a proximal imaging core 106, an impedance matching network 108, a distal imaging core 110, and a rotational transducer 112. In various embodiments, the distal end 118 of elongate member 102 may be inserted into a patient and rotational transducer 112 may be operated by controller 114 to generate radial images within the patient. For example, rotational transducer 112 may be utilized to generate radial ultrasound images within a peripheral airway of a lung. In various embodiments, the outer diameter of the elongate member 102 may be less than 1.5 mm, such as 0.8 mm or 1.2 mm, to facilitate access to peripheral body lumens. For example, the outer diameter of elongate member 102 may be 1.1 mm to facilitate access to peripheral airways. In some embodiments, FIG. 1A may include one or more components that are the same or similar to one or more other components of the present disclosure. Further, one or more components of FIG. 1A, or aspects thereof, may be incorporated into other embodiments of the present disclosure, or excluded from the described embodiments, without departing from the scope of this disclosure. For example, embodiments of medical imaging device 100 may exclude controller 114 without departing from the scope of this disclosure. Still further, one or more components of other embodiments of the present disclosure, or aspects thereof, may be incorporated into one or more components of FIG. 1A, without departing from the scope of this disclosure. Embodiments are not limited in this context.

Figure 1B:
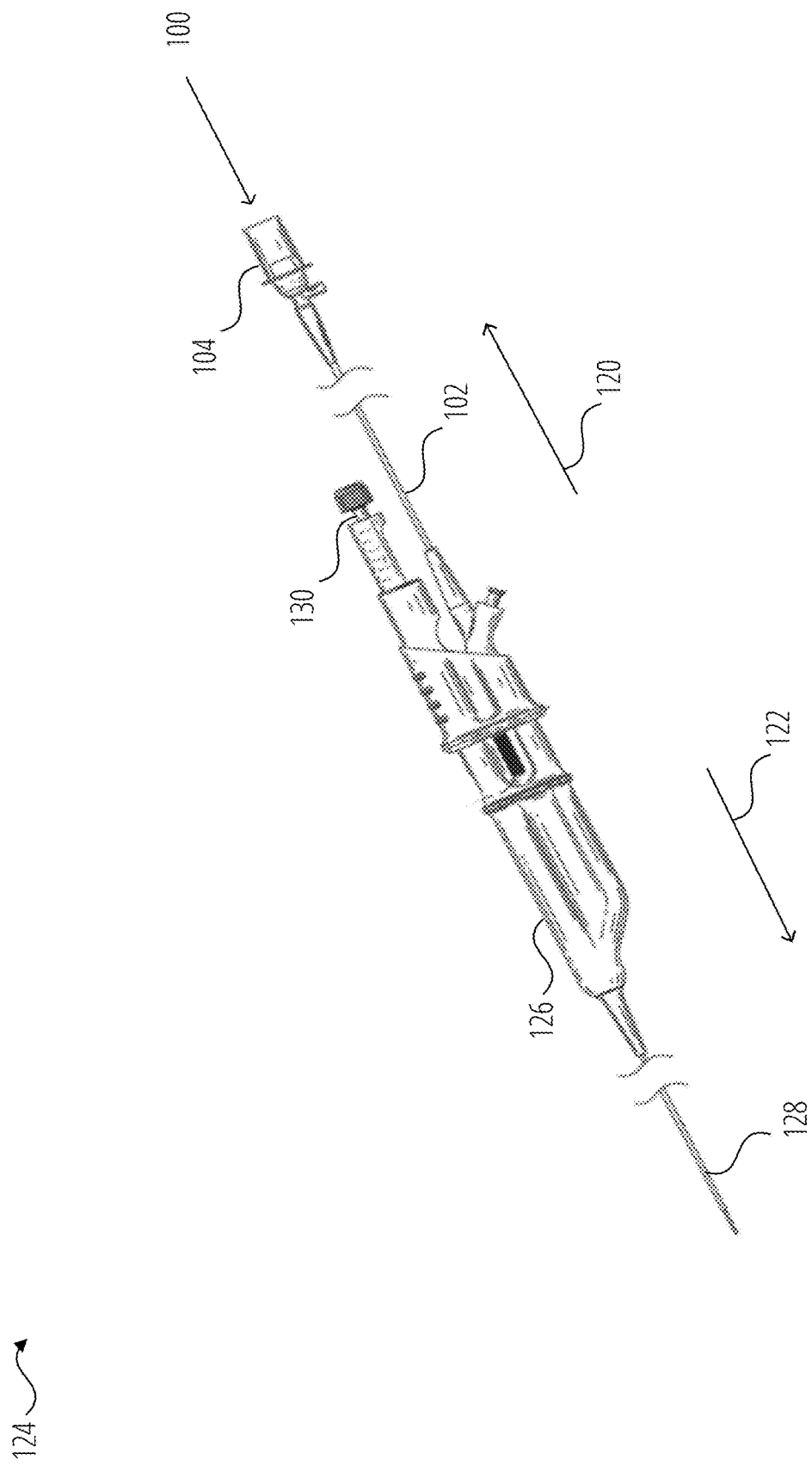
FIG. 1B illustrates an exemplary medical imaging device in conjunction with an exemplary medical device according to one or more embodiments disclosed hereby.

FIG. 1B illustrates medical imaging device 100 in conjunction with a medical device 124 according to one or more embodiments disclosed hereby. The medical device 124 has a proximal end 120, a distal end 122, and includes medical imaging device 100, medical tool 130, handle 126, and dual lumen catheter 128. The illustrated portions of medical imaging device 100 include a portion of elongate member 102 and hub 104. In some embodiments, FIG. 1B may include one or more components that are the same or similar to one or more other components of the present disclosure. Further, one or more components of FIG. 1B, or aspects thereof, may be incorporated into other embodiments of the present disclosure, or excluded from the described embodiments, without departing from the scope of this disclosure. For example, embodiments of medical imaging device 100 may exclude controller 114 without departing from the scope of this disclosure. Still further, one or more components of other embodiments of the present disclosure, or aspects thereof, may be incorporated into one or more components of FIG. 1B, without departing from the scope of this disclosure. Embodiments are not limited in this context.

Various medical imaging devices, or components thereof, described hereby may be used in conjunction with a medical device 124 comprising a dual lumen catheter 128. For example, elongate member 102 may be disposed in a first lumen and medical tool 130 (e.g., a biopsy needle) may be disposed in the second lumen. In such examples, images captured by the rotational transducer 112 may be utilized to guide sample acquisition with the biopsy needle. In some embodiments, application of therapy with an ablation probe may be guided using images captured by the rotational transducer 112. In various embodiments, the outer diameter of the dual lumen catheter may be less than 2 mm, such as 1.5 mm or 1.9 mm.

In the illustrated embodiment of FIG. 1B, the impedance matching network 108 may be disposed in the handle 126.

Accordingly, the proximal imaging core 106 may comprise portions of elongate member 102 proximal of the handle 126 and the distal imaging core 110 may comprise portions of the elongate member 102 distal to the handle 126. Further, the distal imaging core 110 may be disposed in dual lumen catheter 128. In other embodiments, medical imaging device 100 may be used as a stand alone device or in conjunction with an additional, or alternative, device besides the medical device 100. For example, medical imaging device 100 could be inserted through a working channel of one or more of an endoscope, bronchoscope, duodenoscope, gastroscope, colonoscope, ureteroscope, or the like. In some such examples, the dual lumen catheter 128 of medical device 124, with medical imaging device 100 disposed therein, may be inserted through the working channel.

In many embodiments, the dual lumen catheter 128 may be sized to access narrow or peripheral body lumens (e.g., peripheral airways of a lung). In many such embodiments, an elongate member disclosed hereby may enable real-time radial ultrasound imaging to be utilized in conjunction with diagnostic and/or therapeutic tools in a peripheral body lumen (e.g., less than 2 mm). Accordingly, one or more embodiments described hereby may be utilized to improve the quality of images obtained in peripheral body lumens by reducing, removing, or blocking signal noise. Additional exemplary medical devices comprising a dual lumen catheter that may be utilized herein are disclosed in U.S. Non-Provisional patent application Ser. No. 16/875,395, titled "Medical Imaging Devices, Systems, and Methods", filed on May 15, 2020, the entirety of which is incorporated herein by reference.

Figure 2A:
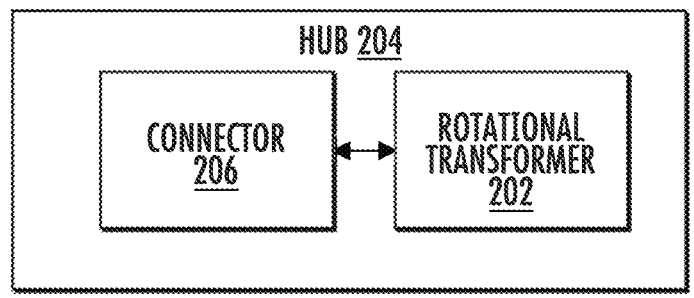
FIG. 2A illustrates an exemplary hub according to one or more embodiments disclosed hereby.

FIG. 2A illustrates a hub 204 according to one or more embodiments disclosed hereby. Hub 204 may include a connector 206 and a rotational transformer 202. In various embodiments, the connector 206 may be utilized to communicatively and conductively couple to a controller (e.g., controller 114). In many embodiments, the rotational transformer 202 may enable communicative and conductive coupling between a rotational transducer (e.g., rotational transducer 112) and a controller (e.g., controller 114) while the transducer is being rotated. In some embodiments, FIG. 2A may include one or more components that are the same or similar to one or more other components of the present disclosure. For example, hub 204 may be the same or similar to hub 104. Further, one or more components of FIG. 2A, or aspects thereof, may be incorporated into other embodiments of the present disclosure, or excluded from the described embodiments, without departing from the scope of this disclosure. For example, connector 206 may be external to hub 204 without departing from the scope of this disclosure. Still further, one or more components of other embodiments of the present disclosure, or aspects thereof, may be incorporated into one or more components of FIG. 2A, without departing from the scope of this disclosure. Embodiments are not limited in this context.

Figure 2B:
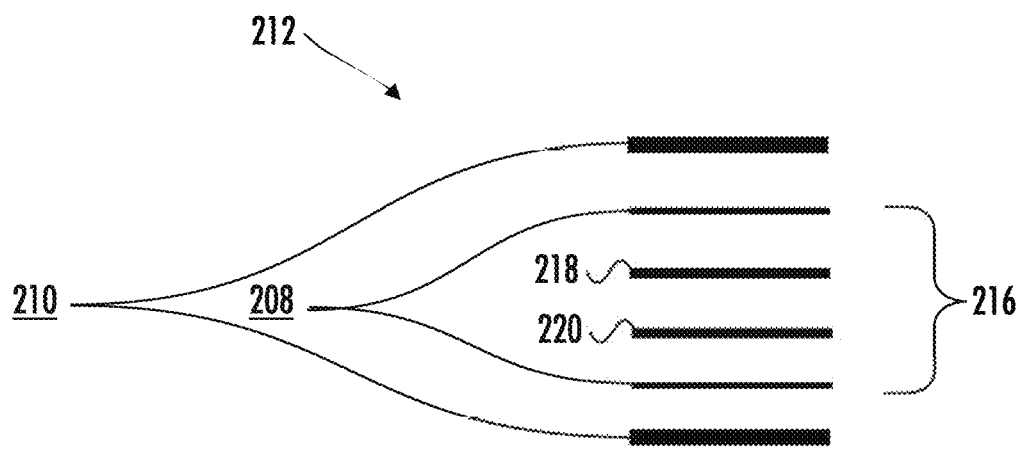
FIG. 2B illustrates an exemplary imaging core according to one or more embodiments disclosed hereby.

FIG. 2B illustrates an imaging core 212 according to one or more embodiments disclosed hereby. Imaging core 212 may include a drive cable 210 and a shielded twisted pair (STP) 216. The STP 216 may include a shield 208, insulated conductor 218, and insulated conductor 220. Generally, imaging core 212 may be used to transmit torque and electrical signals from a proximal end to a distal end. More specifically, the drive cable 210 may transmit torque and the STP 216 may transmit electrical signals. In various embodiments, imaging core 212 may be representative of a proximal imaging core or a distal imaging core. In various such embodiments, the insulated conductors 218, 220 in a proximal imaging core may have a larger diameter than the insulated conductors 218, 220 in a distal imaging core. For example, a proximal imaging core may include a 34-54 American wire gauge (AWG) STP and a distal imaging core may include a 40-60 AWG STP. In another example, the proximal imaging core may include a 42-50 American wire gauge (AWG) STP and a distal imaging core may include a 46-52 AWG STP. In some such examples, the proximal imaging core may provide a 50 ohm impedance to the rotational transformer and the distal imaging core may provide a 75-120 ohm impedance to the rotational transformer. In one embodiment, for instance, the proximal imaging core may include a 50 AWG STP and the distal imaging core may include a 48 AWG STP. In various embodiments, FIG. 2B may include one or more components that are the same or similar to one or more other components of the present disclosure. For example, imaging core 212 may be the same or similar to proximal imaging core 106 and/or distal imaging core 110. Further, one or more components of FIG. 2B, or aspects thereof, may be incorporated into other embodiments of the present disclosure, or excluded from the described embodiments, without departing from the scope of this disclosure. For example, STP 216 may be incorporated into proximal imaging core 106 and/or distal imaging core 110 without departing from the scope of this disclosure. Still further, one or more components of other embodiments of the present disclosure, or aspects thereof, may be incorporated into one or more components of FIG. 2B, without departing from the scope of this disclosure. Embodiments are not limited in this context.

Figure 2C:
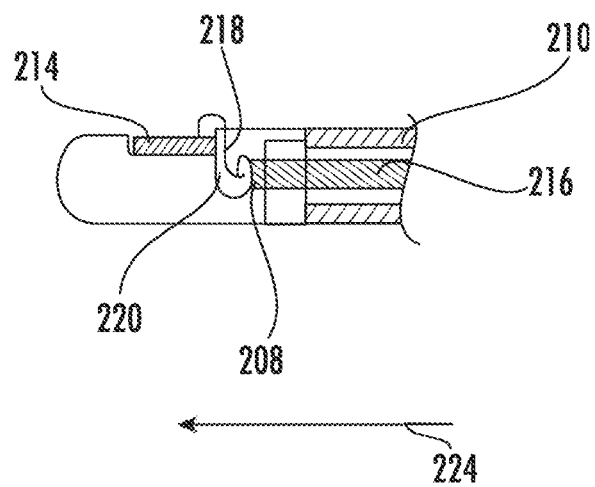
FIG. 2C illustrates an exemplary distal end of an elongate member according to one or more embodiments disclosed hereby.

FIG. 2C illustrates a distal end 224 of an elongate member 222 according to one or more embodiments disclosed hereby. The distal end 224 of elongate member 222 includes drive cable 210, rotational transducer 214, and STP 216 with shield 208, insulated conductor 218, and insulated conductor 220. As shown in the illustrated embodiment, insulated conductors 218, 220 may be coupled to rotational transducer 214. In several embodiments, insulated conductors 218, 220 may be utilized to carry differential signals between the rotational transducer 214 and a controller (e.g., controller 114). In some embodiments, FIG. 2C may include one or more components that are the same or similar to one or more other components of the present disclosure. For example, rotational transducer 214 may be the same or similar to rotational transducer 112. Further, one or more components of FIG. 2C, or aspects thereof, may be incorporated into other embodiments of the present disclosure, or excluded from the described embodiments, without departing from the scope of this disclosure. Still further, one or more components of other embodiments of the present disclosure, or aspects thereof, may be incorporated into one or more components of FIG. 2C, without departing from the scope of this disclosure. For example, impedance matching network 108 may incorporated into elongate member 222 without departing from the scope of this disclosure. Embodiments are not limited in this context.

Figure 3:
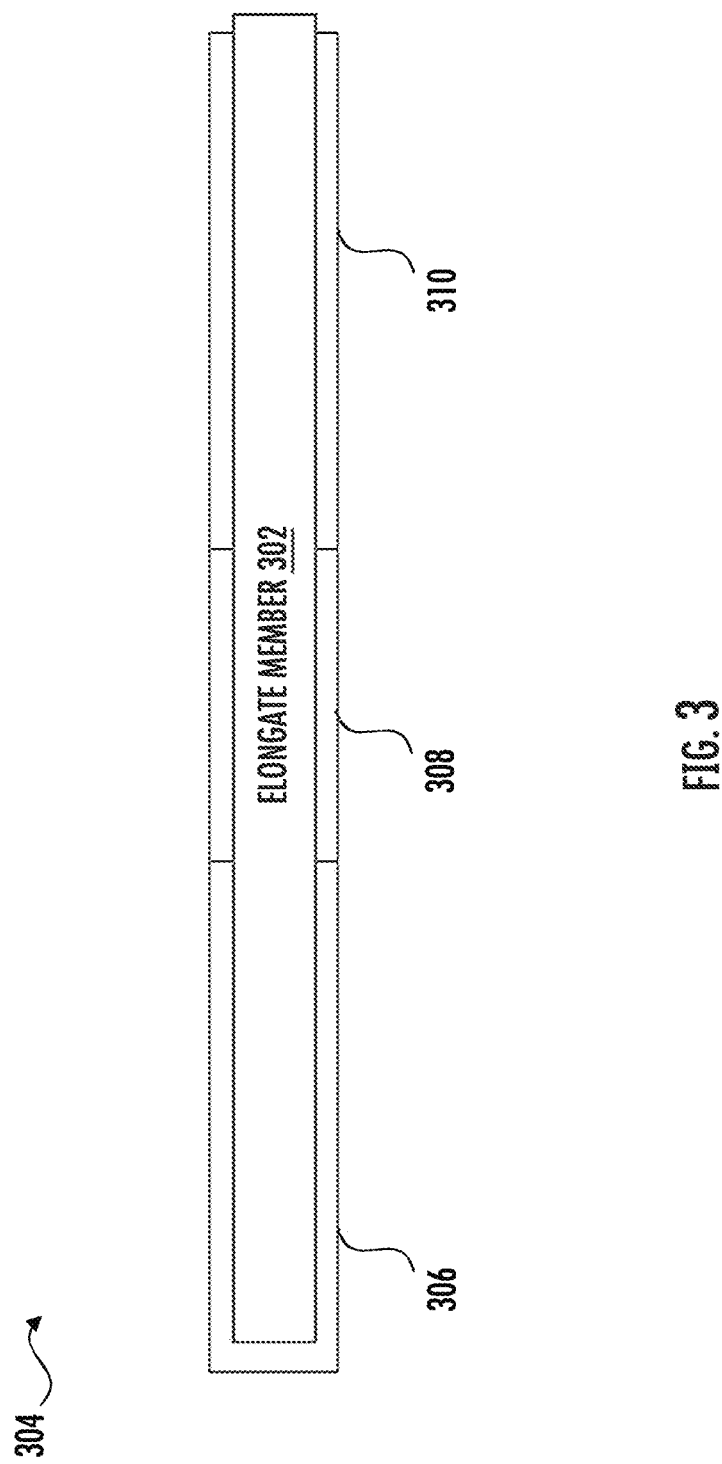
FIG. 3 illustrates an exemplary telescoping sheath according to one or more embodiments disclosed hereby.

FIG. 3 illustrates a telescoping sheath 304 in conjunction with a telescoping sheath elongate member 302. Telescoping sheath 304 (or telescoping catheter) may include distal sheath section 306, telescoping joint 308, and proximal sheath section 310. In various embodiments, telescoping joint 308 may be integrated into distal sheath section 306 and/or proximal sheath section 310. In some embodiments, telescoping sheath 304 may enable selective exposure of one or more portions of elongate member 302. For example, telescoping joint 308 may enable the distal end of elongate member 302 to be extended out of the telescoping sheath 304 and into a body lumen. As will be described in more detail below, in various embodiments, one or more portions of an elongate member (e.g., elongate member 302) may be disposed within telescoping sheath 304. In some embodiments, FIG. 3 may include one or more components that are the same or similar to one or more other components of the present disclosure. For example, elongate member 302 may be the same or similar to elongate member 102. Further, one or more components of FIG. 3, or aspects thereof, may be incorporated into other embodiments of the present disclosure, or excluded from the described embodiments, without departing from the scope of this disclosure. For example, telescoping sheath 304 may be incorporated into medical imaging device 100 without departing from the scope of this disclosure. Still further, one or more components of other embodiments of the present disclosure, or aspects thereof, may be incorporated into one or more components of FIG. 3, without departing from the scope of this disclosure. In various embodiments, sheath and catheter may be used interchangeably. Embodiments are not limited in this context.

Figure 4:
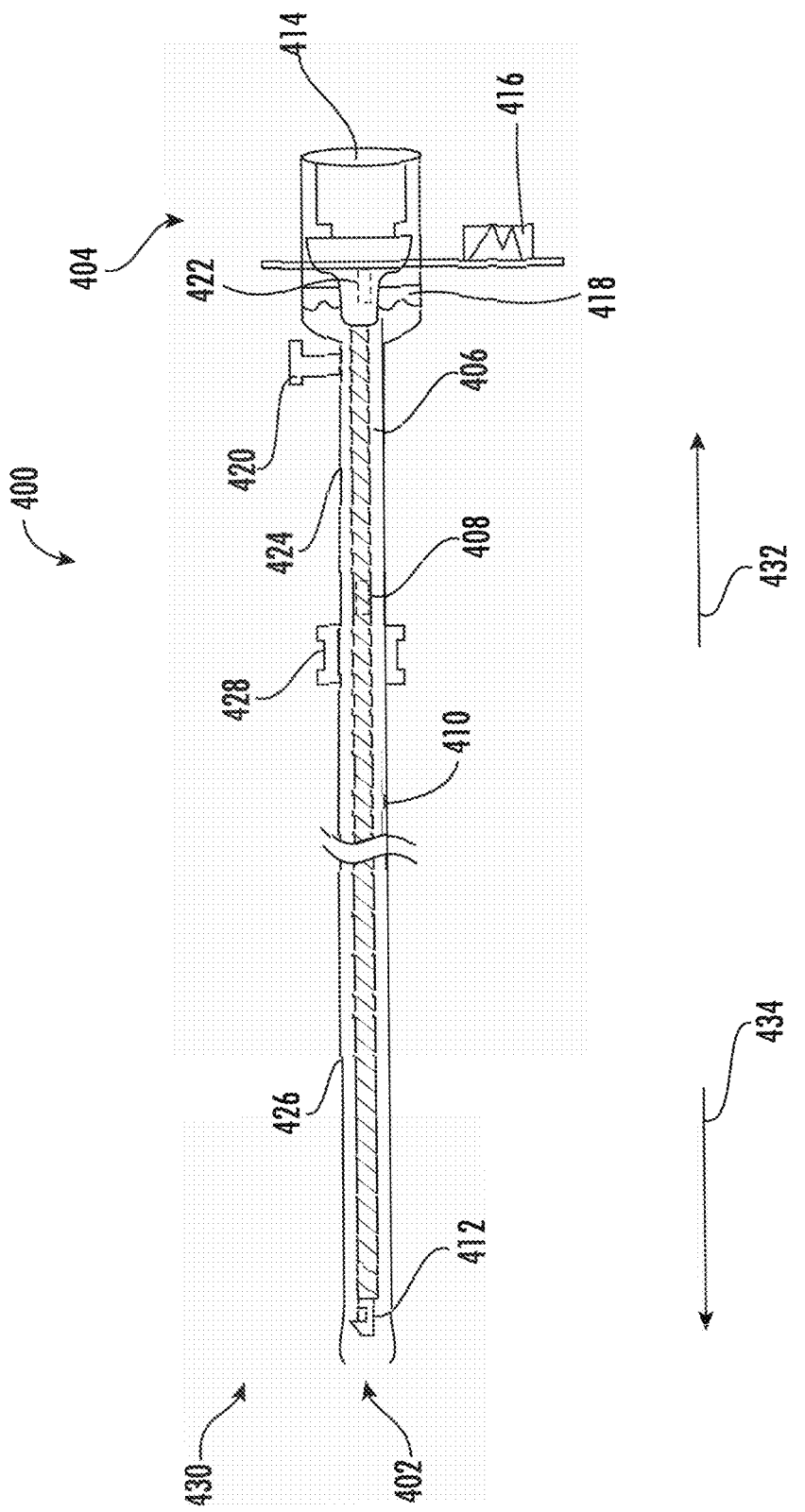
FIG. 4 illustrates an exemplary medical imaging device according to one or more embodiments disclosed hereby.

FIG. 4 illustrates a medical imaging device 400 according to one or more embodiments disclosed hereby. Medical imaging device 400 has a proximal end 432, a distal end 434, and includes elongate member 402 disposed within telescoping sheath 430. In the illustrated embodiments, elongate member 402 includes rotational transducer 412, distal imaging core 410, impedance matching network 408, proximal imaging core 406, hub 404. Hub 404 includes connector 414, identification code board 416, bearing/seal 418, and rotational transformer 422. Telescoping sheath 430 includes distal sheath section 426, telescoping joint 428, and proximal sheath section 424 with flush port 420. In various embodiments, the telescoping sheath 430 may be integrally formed with elongate member 402. In some embodiments, FIG. 4 may include one or more components that are the same or similar to one or more other components of the present disclosure. For example, medical imaging device 400 may be the same or similar to medical imaging device 100. Further, one or more components of FIG. 4, or aspects thereof, may be incorporated into other embodiments of the present disclosure, or excluded from the described embodiments, without departing from the scope of this disclosure. For example, telescoping sheath 430 may be incorporated into medical imaging device 100 without departing from the scope of this disclosure. Still further, one or more components of other embodiments of the present disclosure, or aspects thereof, may be incorporated into one or more components of FIG. 4, without departing from the scope of this disclosure. For example, controller 114 may be incorporated into medical imaging device 400 without departing from the scope of this disclosure. Embodiments are not limited in this context.

In various embodiments, bearing/seal 418 may allow rotation of elongate member 402 while preventing fluids from backing up into rotational transformer 422 or connector 414. For example, a fluid to improve ultrasonic coupling between rotational transducer 412 and a body lumen may be introduced via flush port 420. In such examples, bearing/seal 418 may prevent the fluid from moving proximally past bearing/seal 418. In one or more embodiments, identification code board 416 may include a unique identifier that includes one or more characteristics of medical imaging device 400, or components thereof, such as type of rotational transducer, type of impedance matching network 408, conductor diameters, characteristic impedances, and the like. In one or more such embodiments, the 416 may include a computer-readable memory. In several embodiments, a controller (e.g., controller 114) may connect to identification code board 416 in addition to connector 414. In several such embodiments, the controller may read the contents of identification code board 416.

Figure 5:
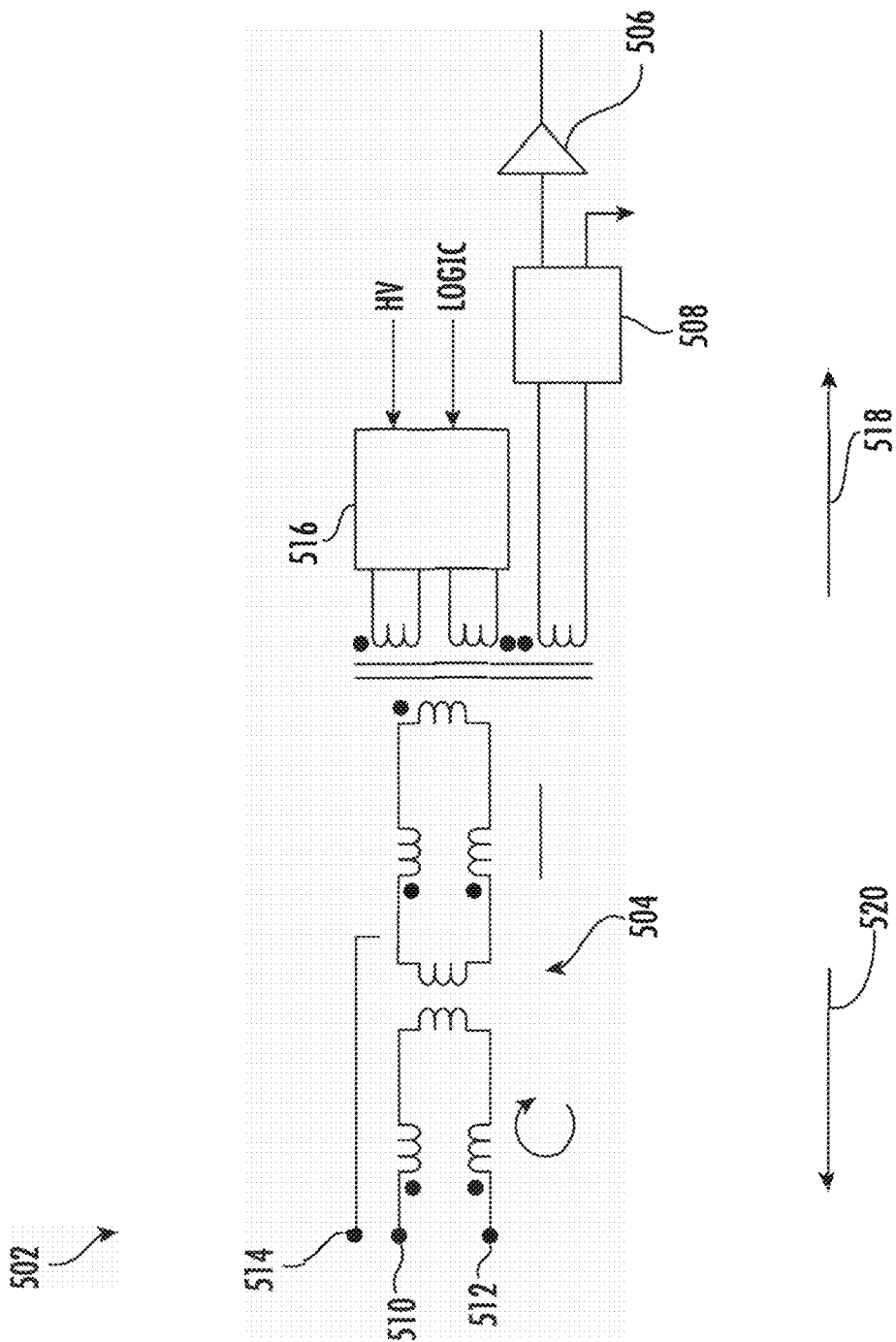
FIG. 5 illustrates an exemplary circuitry according to one or more embodiments disclosed hereby.

FIG. 5 illustrates circuitry 502 according to one or more embodiments disclosed hereby. In various embodiments, circuitry 502 may be included in one or more medical devices and/or elongate members described herein. In the illustrated embodiment, circuitry 502 has a proximal end 518, a distal end 520, and includes rotational transformer 504, insulated conductor 510, insulated conductor 512, shield 514, transmission drivers 516, low noise amplifier 506, and protection circuitry 508. In various embodiments, insulated conductors 510, 512 and shield 514 may comprise, or connect to, an STP (e.g., STP 216). In many embodiments, insulated conductors 510, 512 may carry a differential signal to a rotational transducer (e.g., rotational transducer 112). In several embodiments, transmission drivers 516 may generate signals for insulated conductors 510, 512 based on a high voltage input and a logic input. In one or more embodiments, protection circuitry 508 may monitor signals in the circuitry 502 and implement one or more protective measures (e.g., cut power and/or direct the signal to ground) in response to detecting potentially dangerous signals. In one or more such embodiments, low noise amplifier 506 may operate in conjunction with protection circuitry 508 to generate a signal in response to detection of a potentially dangerous signal by protection circuitry 508. For example, protection circuitry 508 may detect a short between insulated conductors 510, 512 and prevent further damage to components (e.g., rotational transformer 504, transmission drivers 516, controller 114) in response.

In some embodiments, FIG. 5 may include one or more components that are the same or similar to one or more other components of the present disclosure. For example, rotational transformer 504 may be the same or similar to rotational transformer 202. Further, one or more components of FIG. 5, or aspects thereof, may be incorporated into other embodiments of the present disclosure, or excluded from the described embodiments, without departing from the scope of this disclosure. For example, circuitry 502 may be incorporated into elongate member 102 and/or controller 114 without departing from the scope of this disclosure. Still further, one or more components of other embodiments of the present disclosure, or aspects thereof, may be incorporated into one or more components of FIG. 5, without departing from the scope of this disclosure. For example, rotational transducer 412, distal imaging core 410, impedance matching network 408, and proximal imaging core 406 may be incorporated into circuitry 502 (e.g., by connecting proximal imaging core 406 to distal end 520) without departing from the scope of the disclosure. Embodiments are not limited in this context.

Figure 6:
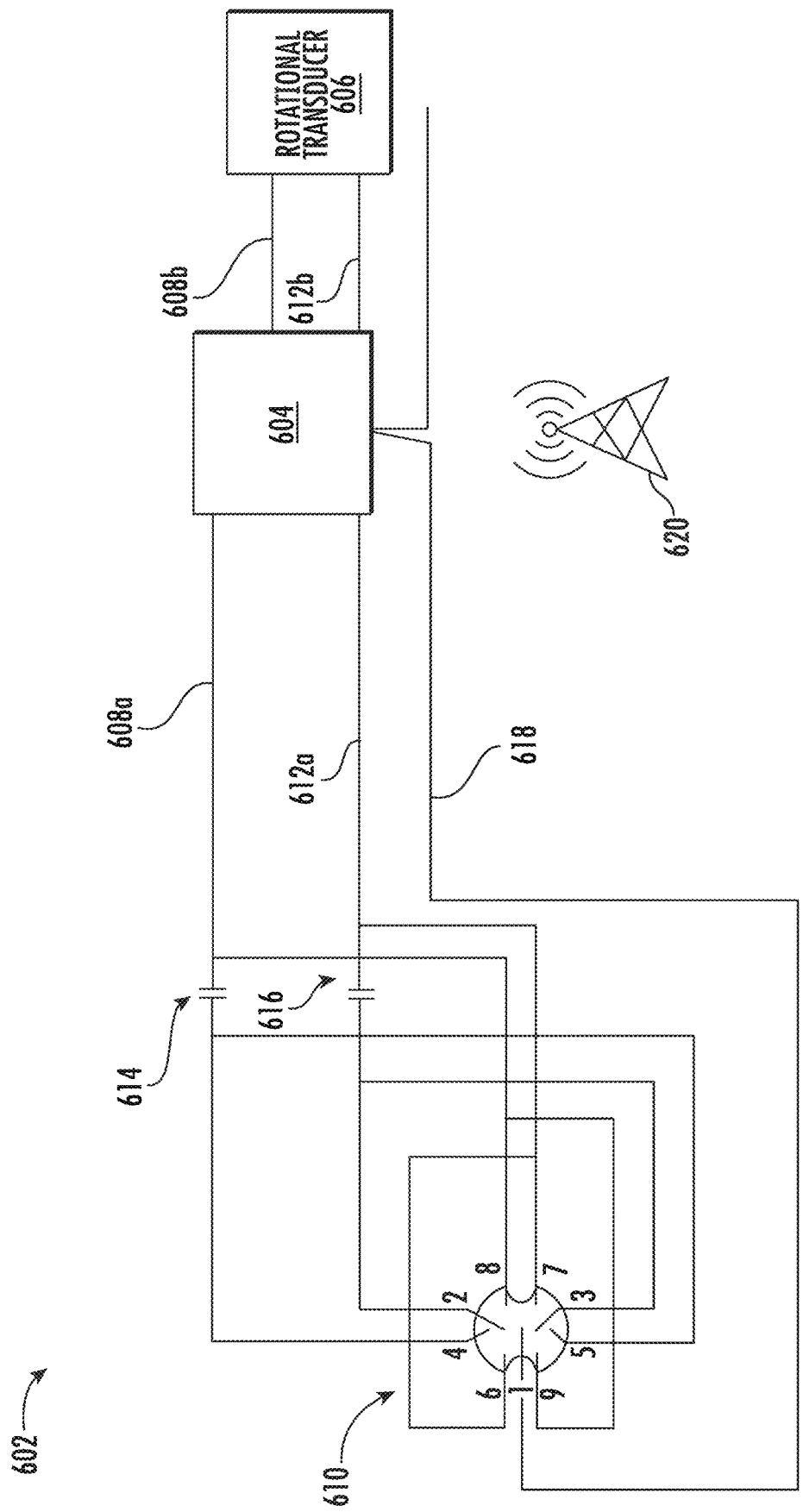
FIG. 6 illustrates an exemplary wiring schematic according to one or more embodiments disclosed hereby.

FIG. 6 illustrates wiring schematic 602 in conjunction with one or more electromagnetic noise source(s) 620 according to one or more embodiments disclosed hereby. In various embodiments, wiring schematic 602 may be included in one or more medical devices, elongate members, and/or controllers described herein. In the illustrated embodiment, wiring schematic 602 includes impedance matching network 604, rotational transducer 606, insulated conductor 608a, 608b, connector 610, insulated conductor 612a, 612b, capacitor 614, capacitor 616, and shield 618. In some embodiments, FIG. 6 may include one or more components that are the same or similar to one or more other components of the present disclosure. For example, connector 610 may be the same or similar to connector 414. Further, one or more components of FIG. 6, or aspects thereof, may be incorporated into other embodiments of the present disclosure, or excluded from the described embodiments, without departing from the scope of this disclosure. For example, electromagnetic noise source(s) 620 may be excluded without departing from the scope of this disclosure. Still further, one or more components of other embodiments of the present disclosure, or aspects thereof, may be incorporated into one or more components of FIG. 6 without departing from the scope of this disclosure. For example, circuitry 502 may be incorporated into wiring schematic 602 without departing from the scope of the disclosure. Embodiments are not limited in this context.

In the illustrated embodiment, connector 610 includes 8 pins. The first pin connects to the shield 618. The second and third pins connect to insulated conductor 612a via capacitor 616. In some embodiments, capacitor 616 may comprise a 200 picofarad (pF) capacitor. In various embodiments, capacitor 616 is rated for 500 volts. The fourth and fifth pins connect to insulated conductor 608a via capacitor 614. In some embodiments, capacitor 614 may comprise a 200 pF capacitor. In various embodiments, capacitor 614 is rated for 500 volts. Further, the second pin may conduct transmit and receive signals for the positive leg of a differential signal and the fourth pin may conduct transmit and receive signals for the negative leg of the differential signal. The sixth and seventh pins connect to insulated conductor 612a. The eighth and ninth pins connect to insulated conductor 608a. Further, the seventh pin may conduct a positive bias signal and the eighth pin may conduct a negative bias signal. In several embodiments, insulated conductors 612a, 612b may carry the positive leg of a differential signal and insulated conductors 608a, 608b may carry the negative leg of the differential signal.

The shield 618 may function to block interference coming from one or more electromagnetic noise source(s) 620. In many embodiments, shield 618 is connected to a reference voltage (e.g., ground). The electromagnetic noise source(s) 620 may include any source of electromagnetic interference. In some embodiments, the electromagnetic noise source(s) 620 includes one or more of hospital bed electronics, wireless communication signals, monitoring devices, pump electronics, infusion devices, imaging devices, and the like.

Figure 7A:
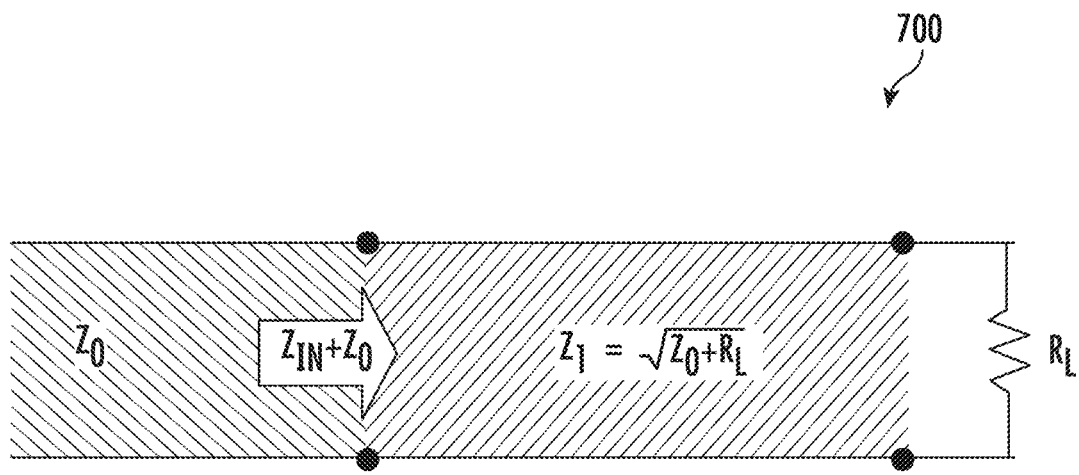
FIGS. 7A and 7B illustrate various aspects of an exemplary impedance matching network according to one or more embodiments disclosed hereby.
Figure 7B:
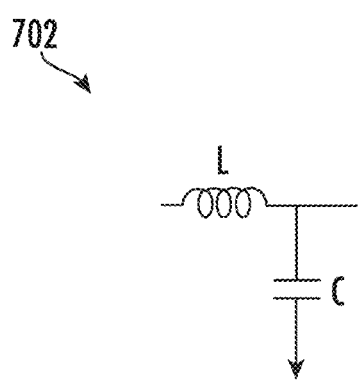

FIGS. 7A and 7B illustrate various aspects of an impedance matching network 700 and inductor-capacitor matching circuit 702 according to one or more embodiments disclosed hereby. In one or more embodiments, a proximal portion of a signal conductor may be coupled to a first end of the inductor and a distal portion of the signal conductor may be coupled to a second end of the inductor. In many embodiments, the inductor and capacitor are electrically connected in parallel. In some embodiments, FIGS. 7A and/or 7B may include one or more components that are the same or similar to one or more other components of the present disclosure. For example, impedance matching network 700 may be the same or similar to impedance matching network 108. Further, one or more components of FIGS. 7A and/or 7B, or aspects thereof, may be incorporated into other embodiments of the present disclosure, or excluded from the described embodiments, without departing from the scope of this disclosure. For example, inductor-capacitor matching circuit 702 may be incorporated into impedance matching network 408 without departing from the scope of this disclosure. Still further, one or more components of other embodiments of the present disclosure, or aspects thereof, may be incorporated into one or more components of FIGS. 7A and/or 7B without departing from the scope of this disclosure. Embodiments are not limited in this context.

In electronics, impedance matching includes the practice of designing the input impedance ($Z_{in}$) of an electrical load to maximize the power transfer or minimize signal reflection from the load. This may be accomplished by matching the input impedance to the characteristic impedance ($Z_O$) of the conductor using impedance matching network 700. In various embodiments described hereby, impedance matching network 700 may be utilized to go from the characteristic impedance of a proximal imaging core to the characteristic impedance of a distal imaging core. For example, the STP of a proximal imaging core may have a 50 ohm characteristic impedance and the STP of a distal imaging core may have a 75 ohm characteristic impedance (with the impedance of the distal imaging core represented by $R_L$). In many embodiments, the higher impedance of the distal imaging core may be attributed to the smaller diameter of the distal STP versus the STP of the proximal imaging core. Accordingly, impedance matching network 700 may be placed between the proximal and distal imaging cores. More specifically, impedance matching network 700 may be placed between the insulated conductors of the proximal and distal imaging cores.

In various embodiments, the impedance matching network 700 may provide an interim impedance to enable a better transition from the proximal imaging core to the distal imaging core. In some embodiments, a separate impedance matching network may be utilized for each signal conductor in an STP. The interim impedance may be determined by multiplying the characteristic impedance of the proximal imaging core by the characteristic impedance of the distal imaging core and then taking the square root. Thus, continuing with the previous example, multiplying 50 ohms for the proximal imaging core by 75 ohms for the distal imaging core and taking the square root results in an interim impedance of approximately 62 ohms. Accordingly, the impedance matching network 700 may be designed with a characteristic impedance of 62 ohms. In many embodiments, the impedance matching network 700 may be designed with a characteristic impedance between 40 and 100 ohms or any subset range thereof (e.g., 50-70 ohms).

In various embodiments, the fundamental frequency of a rotational transducer may be in the 30 MHz range (e.g., for an ultrasound imaging transducer). In some embodiments, a ¼ matched impedance traced engineered balun may be utilized. However, in other embodiments, a ¼ matched impedance traced engineered balun may be impractical due to size constraints. In such other embodiments, an inductor-capacitor matching circuit 702 may be utilized on each leg of the STP (e.g., insulated conductor 218 and insulated conductor 220). Additionally, the shield may be common to ground. In some embodiments, a pi- or tee-network may be utilized. However, in many embodiments, inductor-capacitor matching circuit 702 may be preferred due to requiring only two components as opposed to three components with pi- or tee-networks. At a 30 MHz characteristic impedance, the inductor (L) in inductor-capacitor matching circuit 702 may be 190 nanohenry (nH) and the capacitor (C) may be 50 pF. In some embodiments, the inductor in inductor-capacitor matching circuit 702 may be between 150 and 230 nH (or any range therebetween) and/or the capacitor in 702 may be between 25 and 75 pF (or any range therebetween). In several embodiments, each signal conductor may include a separate impedance matching network. Accordingly, embodiments may include an inductor-capacitor matching circuit 702 for each signal conductor in the proximal and distal imaging cores. In other words, an inductor-capacitor matching circuit may connect proximal portions to distal portions of each signal conductor in the imaging core. For example, embodiments may include an impedance matching network comprising a first inductor and a first capacitor for a first signal conductor and a second inductor and a second capacitor for a second signal conductor. In some such examples, the first signal conductor may correspond to a positive leg of a differential signal and the second signal conductor may correspond to a negative leg of a differential signal.

Figure 8A:
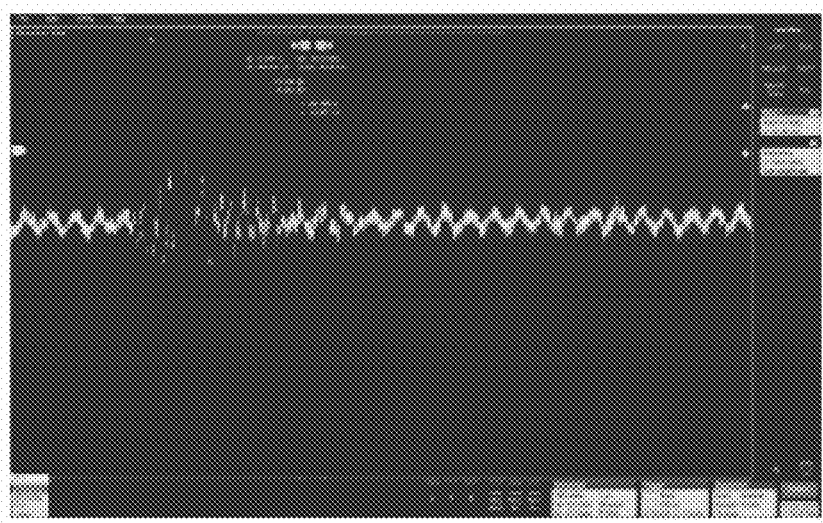
FIGS. 8A-8D illustrate various aspects of imaging signals according to one or more embodiments disclosed hereby.
Figure 8B:
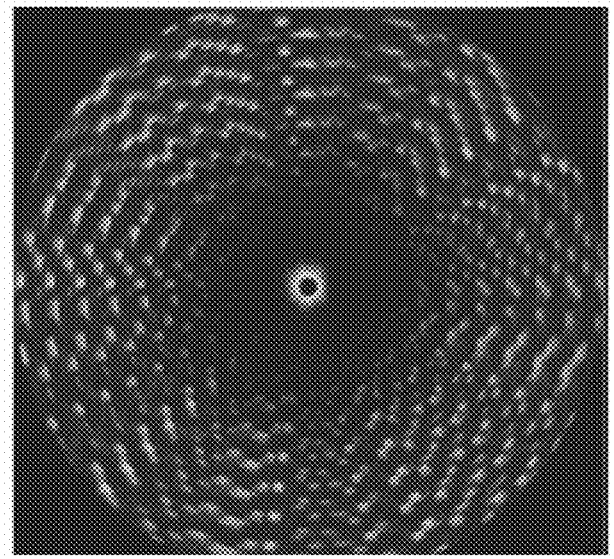
Figure 8C:
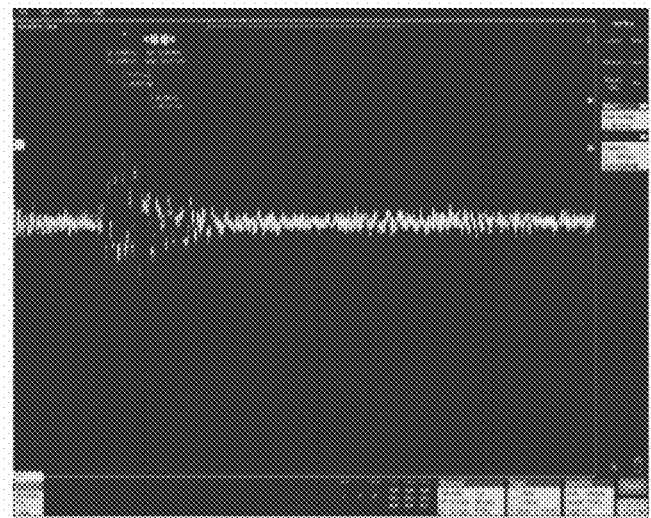
Figure 8D:
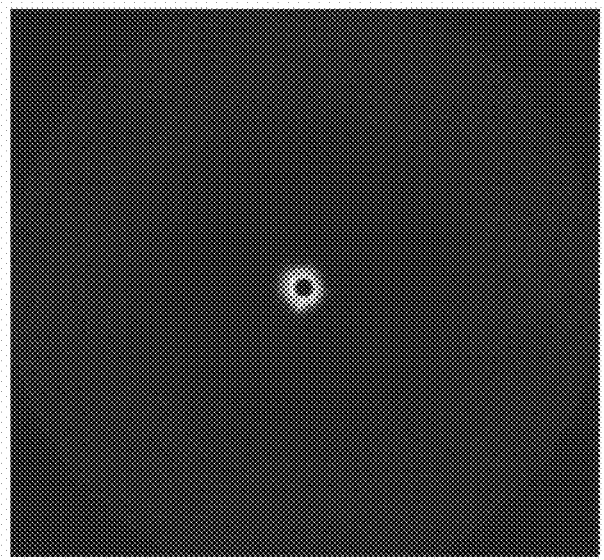

FIGS. 8A-8D illustrate various aspects of imaging signals according to one or more embodiments disclosed hereby. FIG. 8A illustrates a signal with a low signal to noise ratio (SNR) and FIG. 8C illustrates a signal with a high SNR. Further, FIG. 8B illustrates a radial image produced from the signal with the low SNR and FIG. 8D illustrates a radial image produced from a signal with a high SNR. Embodiments are not limited in this context.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

All of the devices and/or methods disclosed and claimed hereby can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit and scope of the disclosure. All such similar substitutes and modifications apparent to those skilled in the art are deemed to be within the spirit, scope and concept of the disclosure as defined by the appended claims.

What is claimed is:
1. A medical imaging device, comprising:
an elongate member configured to access a peripheral airway;
a hub coupled to a proximal end of the elongate member, the hub comprising a connector and a rotational trans- former having first and second ends, the first end coupled to the connector, the connector configured to couple with a controller;

a proximal imaging core disposed in a proximal portion of the elongate member, the proximal imaging core comprising a proximal drive cable and a first shielded twisted pair (STP) of a first diameter, the proximal imaging core having first and second ends, the first end of the proximal imaging core coupled to the second end of the rotational transformer;

a distal imaging core disposed in a distal portion of the elongate member, the distal imaging core comprising a distal drive cable and a second STP of a second diameter different from the first diameter, the distal imaging core having first and second ends, and the second end of the distal imaging core coupled to a rotational imaging transducer; and an impedance matching network disposed in the elongate member, the impedance matching network coupled between the second end of the proximal imaging core and the first end of the distal imaging core, wherein each of the first STP and the second STP comprise a shield and a pair of insulated conductors.

2. The medical imaging device of claim 1, the rotational imaging transducer comprising a rotational ultrasound transducer.

3. The medical imaging device of claim 1, wherein the first STP is disposed within the proximal drive cable and the second STP is disposed within the distal drive cable.

4. The medical imaging device of claim 1, wherein the proximal portion of the elongate member is coupled to the distal portion of the elongate member via a telescoping joint.

5. The medical imaging device of claim 1, wherein the first diameter corresponds to 42-50 American wire gauge (AWG) and the second diameter corresponds to 46-53 American wire gauge.

6. The medical imaging device of claim 1, wherein the proximal imaging core, the distal imaging core, and the impedance matching network are disposed within a telescoping sheath.

7. The medical imaging device of claim 1, wherein the impedance matching network comprises an inductor and a capacitor electrically connected in parallel.

8. The medical imaging device of claim 7, wherein the inductor is between 170 and 210 nanohenry and the capacitor is between 40 and 60 picofarad.

9. The medical imaging device of claim 1, wherein the impedance matching network comprises a characteristic impedance between 55 and 75 ohms.

10. The medical imaging device of claim 1, wherein the distal imaging core includes a plurality of signal conductors and the impedance matching network includes an inductor-capacitor matching circuit for each of the plurality of signal conductors.

11. The medical imaging device of claim 1, wherein the elongate member has a diameter between 0.8 millimeters (mm) and 1.2 mm.

12. A system, comprising:
an elongate member configured to access a peripheral airway;
a hub coupled to a proximal end of the elongate member, the hub comprising a connector and a rotational transformer having first and second ends, the first end coupled to the connector;
a controller coupled to the connector;
a proximal imaging core disposed in a proximal portion of the elongate member, the proximal imaging core comprising a proximal drive cable and a first shielded twisted pair (STP) of a first diameter, the proximal imaging core having first and second ends, the first end of the proximal imaging core coupled to the second end of the rotational transformer;

a distal imaging core disposed in a distal portion of the elongate member, the distal imaging core comprising a distal drive cable and a second STP of a second diameter different from the first diameter, the distal imaging core having first and second ends, and the second end of the distal imaging core coupled to a rotational imaging transducer; and an impedance matching network disposed in the elongate member, the impedance matching network coupled between the second end of the proximal imaging core and the first end of the distal imaging core, wherein each of the first STP and the second STP comprise a shield and a pair of insulated conductors.

13. The system of claim 12, wherein the impedance matching network comprises an inductor between 170 and 210 nanohenry and a capacitor between 40 and 60 picofarad.

14. The system of claim 12, wherein the impedance matching network comprises a characteristic impedance between 55 and 75 ohms.

15. The system of claim 12, wherein the impedance matching network includes a first inductor-capacitor matching circuit for first insulated conductors of the pair of insulated conductors of the first STP and the second STP and a second inductor-capacitor matching circuit for second insulated conductors of the pair of insulated conductors of the first STP and the second STP.

16. The system of claim 12, wherein the elongate member has a diameter between 0.8 millimeters (mm) and 1.2 mm.

17. A method, comprising,
inserting an elongate member into a peripheral airway, the elongate member comprising a hub, a distal imaging core, a proximal imaging core, and an impedance matching network disposed therein,
wherein the hub comprises a rotational transformer,
wherein the proximal imaging core has first and second ends and comprising a proximal drive cable and a first shielded twisted pair (STP) of a first diameter, the first end of the proximal imaging core coupled to the rotational transformer and the second end of the proximal imaging core coupled to the impedance matching network, and
wherein the distal imaging core has first and second ends and comprising a distal drive cable and a second STP of a second diameter different from the first diameter, the second end of the distal imaging core coupled to a rotational imaging transducer, the first end of the distal imaging core coupled to the impedance matching network; and
generating a radial image with the rotational imaging transducer,
wherein each of the first STP and the second STP comprise a shield and a pair of insulated conductors.

18. The method of claim 17, wherein the impedance matching network comprises an inductor between 170 and 210 nanohenry and a capacitor between 40 and 60 picofarad.

19. The method of claim 17, wherein the impedance matching network comprises a characteristic impedance between 55 and 75 ohms.

20. The method of claim 17, wherein the impedance matching network includes a first inductor-capacitor matching circuit for first insulated conductors of the pair of insulated conductors of the first STP and the second STP and a second inductor-capacitor matching circuit for second insulated conductors of the pair of insulated conductors of the first STP and the second STP.

* * * * *